United States Patent
Elson et al.

(10) Patent No.: US 6,566,397 B2
(45) Date of Patent: May 20, 2003

(54) ACYCLIC ISOPRENOID ETHER DERIVATIVES AS CHEMOTHERAPEUTICS

(75) Inventors: Charles E. Elson, Madison, WI (US); Manfred Jung, Munster (DE); Huanbiao Mo, Denton, TX (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 09/906,521

(22) Filed: Jul. 16, 2001

(65) Prior Publication Data

US 2002/0045584 A1 Apr. 18, 2002

Related U.S. Application Data

(60) Provisional application No. 60/219,249, filed on Jul. 18, 2000.

(51) Int. Cl.[7] .................. A61K 33/35; C07D 311/74
(52) U.S. Cl. .................. 514/532; 514/544; 514/529; 514/546; 514/722; 514/670; 514/717; 514/718; 549/398; 549/401; 549/404
(58) Field of Search .................. 514/546, 722, 514/532, 670, 717, 718, 544, 529; 549/398, 401, 404

(56) References Cited

U.S. PATENT DOCUMENTS

5,466,718 A * 11/1995 Nakatsu et al. .............. 514/724
5,567,729 A * 10/1996 Bradfute et al. ............. 514/546
6,303,654 B1 * 10/2001 Elson et al. ................. 514/535

FOREIGN PATENT DOCUMENTS

| JP | 05070439 | * | 3/1993 |
| WO | WO 98/38993 | | 9/1998 |
| WO | WO 99/45912 | * | 9/1999 |

OTHER PUBLICATIONS

Bryant et al., "Physiological genetics of melanotic tumors in *Drosphila melanogaster*. VI. Tumorigenic effects of juvenile hormonelike substances" Genetics, 62(2), pp. 321–336, 1969.*

J.H. Marriott, et al., Synthesis of the Farnesyl Ether 2,3, 5–trifluoro–6–hydroxy–4–(E,E)–3,7–11–trimethyldo-doca–2,6,10 . . . J. Chem. Soc., Perkin Trans 1:4265–4278 2000.

H. Mo and C. Elson, "Apoptosis and Cell–Cycle Arrest in Human and Murine Tumor Cells are Initiated by Isoprenoids," Am. Soc. Nut. Sci., pp. 804–813, 1999.

H. Mo, et al., "Farnesyl Anthranilate Suppresses the Growth, In Vitro and In Vivo, of Murine B16 Melanomas," Cancer Letters 157:145–153, 2000.

J.H. Marriott, et al., "Synthesis of the Farnesyl Ether 2,3, 5–trifluoro–6–hydroxy–4–[(E,E) –3,7,11–trimethyl-dodeca–2,6,10–trien–1–yloxy] nitrobenzene, and Related Compounds Containing a Substituted Hydroxytrifluorophe-nyl Residue: Novel Inhibitors of Protein Farnesyltrans-ferase, Geranylgeranyltransferase I and Squalene Synthase," J. Chem. Soc. 1:4265–4278, 2000.

H. Mo, et al., "Blends of Farnesol and Genistein Synergis-tically Suppress B16 Melanoma Cell Proliferation," FASEB J. 15:A281, 2001 (abstract).

* cited by examiner

*Primary Examiner*—Samuel Barts
*Assistant Examiner*—Devesh Khare
(74) *Attorney, Agent, or Firm*—Quarles & Brady LLP

(57) ABSTRACT

A method of and compositions for suppressing the growth of tumor cells in a patient are disclosed. In one embodiment, the method comprises treating the patient with an effective amount of an isoprenoid ether-linked compound, wherein the isoprenoid ether-linked compound comprises a first acyclic isoprenoid molecule linked via an ether linkage to a second molecule, wherein the second molecule can suppress tumor formation.

14 Claims, 8 Drawing Sheets

| COMPOUND | STRUCTURE | IC50 (umol/L, B16) | IC50 (umol/L, HL60) |
|---|---|---|---|
| M363 | (structure) | 5.1 ± 0.8 | 8.6 ± 2.3 |
| M364 | (structure) | 2.0 ± 0.6 | 4.5 ± 1.8 |
| FARNESYL ANTHRANILATE | (structure) | 45 ± 6 | 80 ± 10 |

| COMPOUND | STRUCTURE | IC50 (umol/L, B16) | IC50 (umol/L, HL60) |
|---|---|---|---|
| M363 | 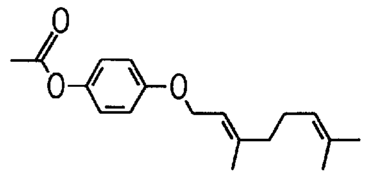 | 5.1±0.8 | 8.6±2.3 |
| M364 | 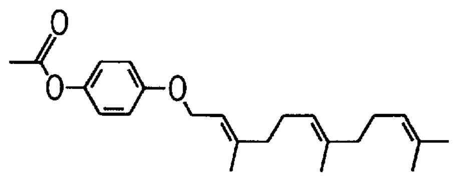 | 2.0±0.6 | 4.5±1.8 |
| FARNESYL ANTHRANILATE | 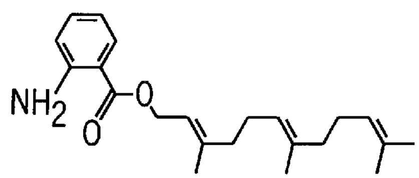 | 45±6 | 80±10 |

FIG. 1

ACYCLIC ISOPRENOID ETHER DERIVATIVES AS CHEMOTHERAPEUTICS

CROSS-REFERENCE TO RELATED APPLICATION

This application claims priority to U.S. Ser. No. 60/219,249, filed Jul. 18, 2000, incorporated by reference herein.

STATEMENT REGARDING FEDERALLY SPONSORED RESEARCH OR DEVELOPMENT

BACKGROUND OF THE INVENTION

Farnesol activates a microsomal cysteine protease with high specificity for HMG CoA reductase (Correll, C. C., et al., *J. Biol. Chem.* 269:17390–17393, 1994; Meigs, T. E., et al., *J. Biol. Chem.* 271:7916–7922, 1996). As a consequence, the cellular pool of mevalonic acid becomes limiting for cell proliferation. Neoplastic cells have much greater sensitivity than normal cells to farnesol-mediated actions (Adany, I., et al. *Cancer Lett.* 79:175–179, 1994; Yazlovitskaya E. M. and Melnykovych, G., *Cancer Lett.* 88:179–183, 1995).

Diet studies show that farnesol (90 mmol/kg diet) suppressed the growth of pancreatic tumors implanted in Syrian Golden hamsters (Burke, et al., *Lipids* 32:151–156, 1997). The elevation of farnesol is short-lived as cytosolic prenyl alcohol dehydrogenase and microsomal oxidase activities convert farnesol to α-, ω-prenyl dioic acids which are excreted (Christophe, J. and Popjak, G., *J. Lipid Res.* 2:244–257, 1961; Gonzalez-Pacanowska, D. G., et al., *J. Biol. Chem.* 263:1301–1306, 1988). He, et al. (He, L., et al., *J. Nutr.* 127:668–674, 1997) reported findings that γ-tocotrienol, a farnesol mimetic, suppressed the growth of implanted melanomas with nearly 100×greater efficacy than farnesol (<1 mmol/kg diet). When coupled with the tocol ring the farnesyl moiety is not converted to the prenyl acids and thus is not excreted.

BRIEF SUMMARY OF THE INVENTION

In one embodiment, the present invention is a method of suppressing the growth of tumor cells in a patient, comprising treating the patient with an effective amount of an isoprenoid ether-linked compound, wherein the isoprenoid ether-linked compound comprises a first acyclic isoprenoid molecule linked via an ether linkage to a second molecule, wherein the second molecule can suppress tumor formation. Preferably, the second molecule comprises a cyclic isoprenoid or hydroxyphenol acetate.

In another embodiment the second molecule is selected from the group consisting of flavonols, isoflavonols and polyphenols and substituted hydroquinones.

In another embodiment, the present invention is a chemotherapeutic compound comprising an acyclic isoprenoid alcohol linked via an ether linkage to a cyclic isoprenoid alcohol or 4-hydroxyphenyl acetate and a pharmaceutical carrier.

In another embodiment, the present invention is a chemotherapeutic compound comprising M364 and a pharmaceutical carrier.

It is a feature of the present invention that a chemotherapeutic compound is provided.

It is an object of the present invention to treat tumor patients by ingestion of an acyclic isoprenoid ether linked compound.

Other objects, features and advantages of the present invention will become apparent to one of skill in the art after review of the specification, claims and drawings.

DETAILED DESCRIPTION OF THE SEVERAL VIEWS OF THE DRAWINGS

FIG. 1 is a schematic diagram of M363, M364 and farnesyl anthranilate.

FIGS. 4A–E is a set of 100×photomicrograph of melanoma B16 cells incubated with farnesyl anthranilate (A–E is 0–100 μmol/L). FIG. 4F is a 400×magnification of cells incubated with 100 μmol/L farnesyl antranilate.

Figure 5:
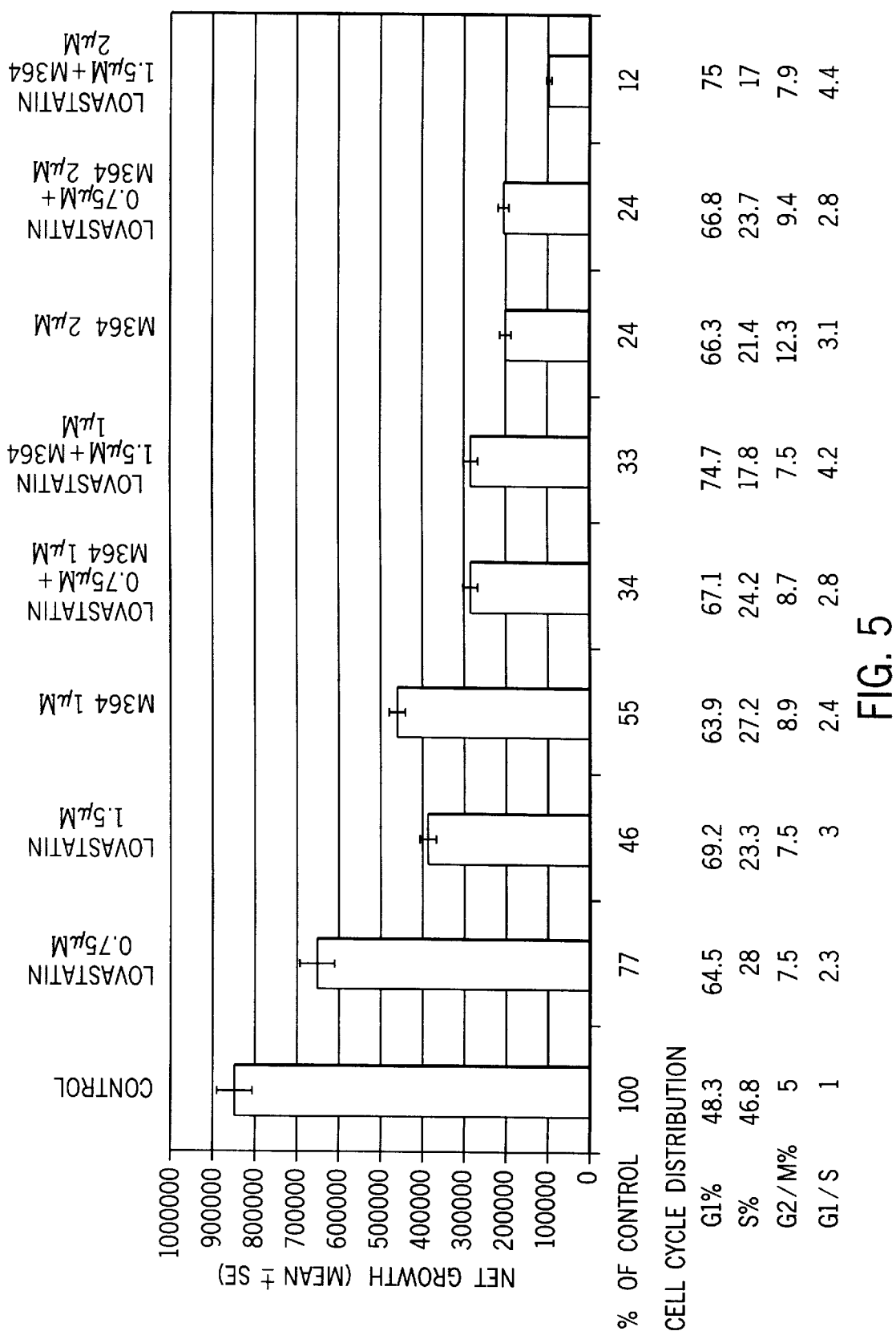

FIG. 5 shows the impact of M364 and lovastatin individually and in combination on the growth and cell cycle distribution of murine B16 melanoma cells.

Figure 6:
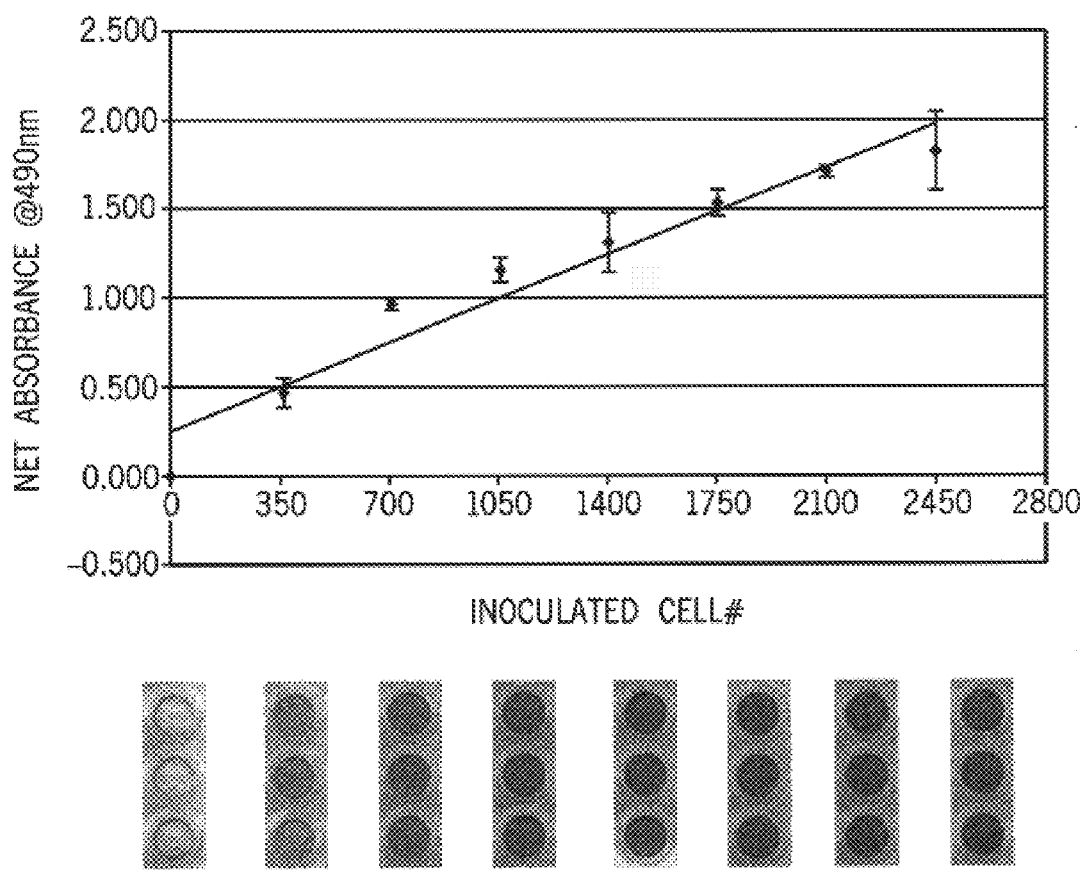

FIG. 6 is a graph of net absorbance at 490 nm versus inoculated cell.

Figure 7:
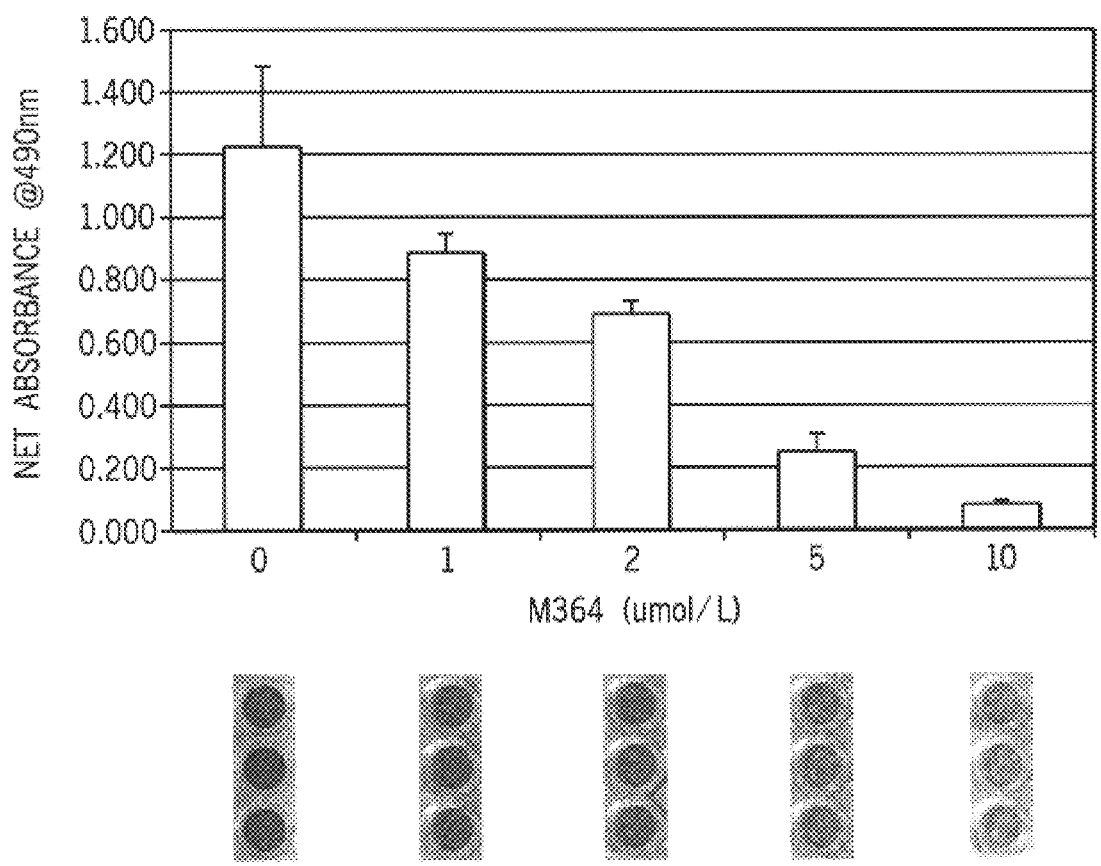

FIG. 7 is a bar graph demonstrating dose-dependent impact of M364 on net absorbance at 490 nm, an indicator of net cell growth.

Figure 8A:
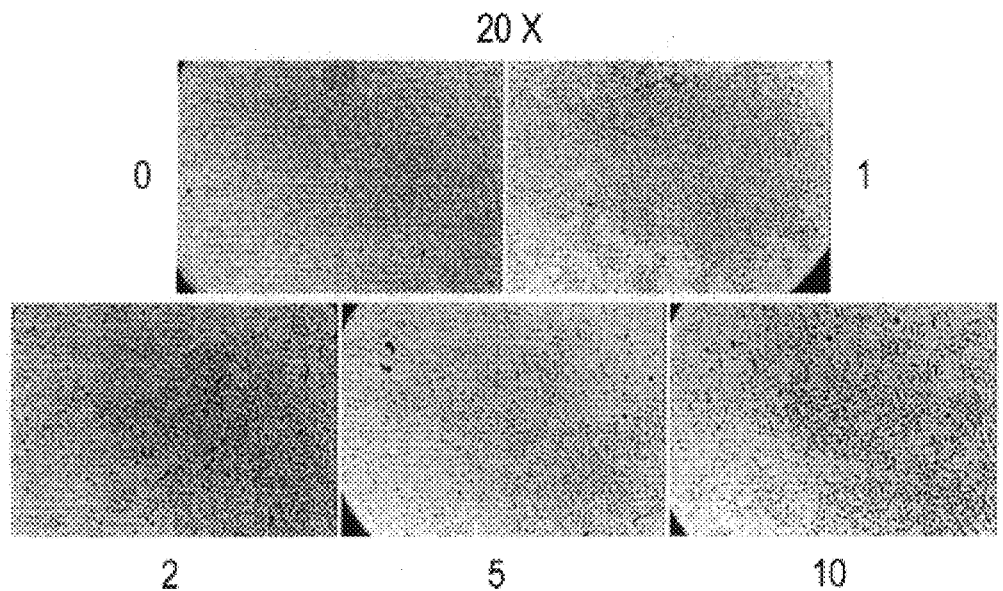
Figure 8B:
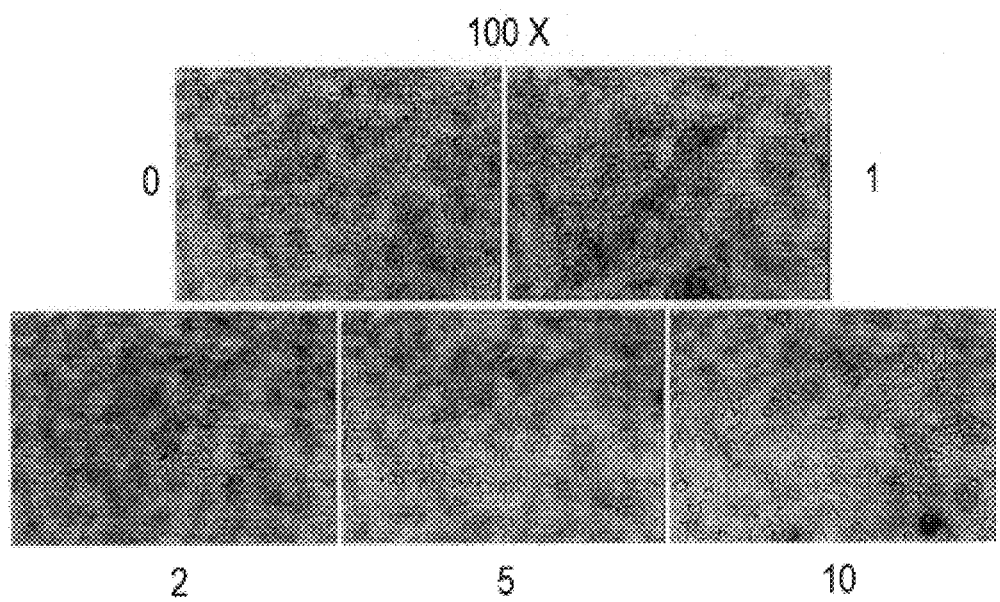

FIG. 8 is a set of photomicrographs of B16 melanoma cells showing the impact of M364 on their growth. FIG. 8A is a 20×magnification, and FIG. 8B is a 100×magnification.

DESCRIPTION OF THE INVENTION

We synthesized and tested a series of esters formed between acyclic isoprenoid alcohols (geraniol, farnesol, nerol, citronellol) and diverse acids (proprionate, isobutyrate, formate, butyrate, caprylate, isovalerate, benzoate, tiglate, anthranilate). Of these, geranyl benzoate, geranyl tiglate, geranyl anthranilate, farnesyl benzoate, farnesyl tiglate and farnesyl anthranilate were deemed to have significant tumor-suppressive activity in vitro. See Mo, et al. *Cancer Letters* 157:145–153, 2000 (incorporated by reference). We found that 1.5 mmol farnesyl anthranilate/kg diet substantially suppressed the growth of implanted B16 melanomas.

We note that the farnesyl moiety of the test agent comprised trans, trans and cis, trans isomers. The trans, trans isomer affords the more potent tumor-suppressive activity. γ-Tocotrienol, a trans, trans farnesyl mimetic (0.116 mmol/kg diet), suppressed the growth of implanted B16 melanomas (He, L., et al., *J. Nutr.* 127:668–674, 1997). The prospect of a chemotherapeutic application of α-tocotrienol is dimmed by findings that its very potent tumor-suppressive action is markedly attenuated by α-tocotrienol, an essential dietary constituent (Qureshi, A., et al., *J. Nutr.* 126:389–394, 1996).

Contrary to findings with γ-tocotrienol, dietary α-tocopherol did not compromise the farnesyl anthranilate action. The ester bond formed between farnesol and anthranilate is cleaved by constitutive non-specific esterases, thereby rendering the head group of farnesol available to oxidative degradation.

The present invention begins with our postulation that a farnesyl derivative formed with an ether bond would be resistant to esterase activity and thus protected from degradation and excretion. Additionally, we envision that the secondary member of the ether could in itself provide tumor-suppressive activity. Therefore, the present invention comprises isoprenoid ether derivatives and the use of these derivatives as chemotherapeutics. Preferably, the isoprenoid ether derivatives comprise an acyclic isoprenoid (preferably selected from the group consisting of geraniol, farnesol, nerol and citronellol) coupled by way of an ether linkage to a cyclic isoprenoid with a known tumor-suppressive activity (e.g., perillyl alcohol). However, we envision that ethers formed using a tumor-suppressive compound which is not a cyclic isoprenoid, hydroxy phenylacetate for example (Thibault, A., et al., *Cancer* 75:2932–2938, 1995), and an acyclic isoprenoid would also be suitable.

Two compounds, one a cyclic isoprenoid, perillyl alcohol, and the second 4-hydroxyphenyl acetate were considered. We opted to synthesize geranyl and farnesyl ethers using the latter. M363 refers to the geranyl ether, [4(3,7-dimethyl-2,6-octadienyloxy]-phenyl acetate and M364 to the farnesyl ether, [4-(3,7,11-trimethyl-2,6,10-dodecatrienyloxy]-phenyl acetate. (See FIG. 1). Other compounds that we believe would be especially effective are the geranyl/farnesyl ethers formed with diverse flavonols, isoflavanols, polyphenols and substituted hydroquinones.

One would use the compounds of the present invention as chemotherapeutics in a manner consistent with other chemotherapeutic agents. Determination of an $IC_{50}$ for each individual compound will give one of skill in the art information as to the amount of the compound that should be consumed or introduced into the tumor patient. Preferred administration is oral.

M364 is preferably synthesized in the following manner:

Farnesol (0.15 mL, 222 mg, 1 mmol), hydroquinone monoacetate (152 mg, 1 mmol) and tributylphosphine (0.25 mL, 202 mg, 1 mmol) are dissolved in 10 mL of dry THF. Diethyl diazocarboxylate (0.16 mL, 174 mg, 1 mmol) are added dropwise and the mixture is stirred for 16 hours at room temperature. The solvent is then removed at reduced pressure and the resulting oil is purified twice by column chromatography (hexane/ethyl acetate 20/1, v/v; then pentane/methyl acetate 20/1, v/v). The product is obtained as a clear oil 120 mg, 34% yield).

Purity and identity are typically assessed by NMR.

1H NMR (CDCl3): 7.26–6.96 (m, 2H, 2-H, 6-H), 6.93–6.87 (m, 2H, 3-H, 5-H), 5.53–5.45 (m, 1H, 2=B4-H), 5.12–5.07 (m, 2H, 6=B4-H, 10=B4-H), 4.52 (d, 2H, J=3D 5.7 Hz, OCH2), 2.28 (s, 3H, COCH3), 2.20–1.93 (m, 8H, CH2CH2), 1.73 (d, 3H, 4J=3D 0.6 Hz, CH3), 1.69 (d, 3H, 4J=3D 0.8 Hz, CH3), 1.61 (s, 6H, 11=B4-CH3).

13C NMR (CDCl3): 169.83 (CO), 156.73 (C-4), 144.32 (C-1), 141.34 (C-3=B4), 135.55 (C-7=B4), 131.35 (C-11=B4), 124.47, 123.81 (C-6=B4, C-10=B4), 122.29 (C-2/C-6), 119.62 (C-2=B4), 115.42 (C-3/C-5), 65.44 (OCH2), 39.80, 39.65 (C-4=B4, C-8=B4), 26.86, 26.37 (C-5=B4, C-9=B4), 25.74 (C-12=B4), 21.11 (COCH3), 17.76, 16.74, 16.12 (3=B4-CH3, 7=B4-CH3, 11=B4-CH3).

EXAMPLES

Screening of M363 and M364 for Tumor-suppressive Activity

The ethers depicted in FIG. 1 were screened for tumor-suppressive activity as described below:

Murine B16 F10 melanoma cells (He, L., et al., supra, 1997) were grown in monolayer culture (35×10 mm tissue culture dishes) in 3 ml RPMI 1640 medium (Sigma Biosciences, St. Louis, Mo.) supplemented with 10% fetal bovine serum (FBS, Sigma Biosciences) and 2% penicillin/streptomycin (Penicillin-Streptomycin Liquid, $1 \times 10^7$ units penicilin and $1 \times 10^7$ μg streptomycin/L of 0.85% saline, GIBCO BRL, Grand Island, N.Y.). Cultures, seeded with $3.3 \times 10^4$ cells/mL, were incubated for 24 hours at 37° C. in a humidified atmosphere of 5% $CO_2$. The medium was decanted and replaced with fresh medium containing the test agents and incubations were continued for 48 hours. M363 and M364 were dissolved in ethanol, and lovastatin (Mevinolin, Sigma) in chloroform. All cultures contained 5 ml ethanol/L (80 mmol/L); chloroform at concentrations to 60 mmol/L had no impact on cell growth. The medium and detached (apoptotic) cells were decanted, the monolayer was washed twice with Hanks' Balanced Salt Solution (HBSS, Sigma Biosciences) and then incubated with a trypsin-EDTA solution (Sigma Biosciences) at 37° C. for 2 minutes. Trypsin was inactivated by suspending the cells in medium containing 10% FBS. The trypsinized cells were harvested by centrifugation (250×g) and re-suspended in HBSS. Viable cells, cells that excluded 0.4% trypan blue (GIBCO BRL), were counted with a hemocytometer; 0-time (24-h) cell counts were deducted from final cell counts to provide an estimate of the net increase in cell number.

Photomicrographs (100×, 200× and 400×) of representative fields of cultures of B16 melanoma cells were made with a Labopot-2 microscope (Nikon, Japan) equipped with a SenSys digital camera (Photometrics Tucson, Ariz.) and image-acquisition software (MetaMorph Imaging Systems, Universal Imaging Corporation, West Chester, Pa.).

Human HL-60 acute promyelocytic leukemia cells (CCL-240, ATCC) were grown in suspension culture (25 cm² flasks) in 8 mL RPMI 1640 medium with 20% FBS and 2% penicillin/streptomycin. Cultures, seeded with $1.25 \times 10^8$ cells/L, were incubated with test agents for 24 hours at 37° C. in a humidified atmosphere of 5% $CO_2$. The cells were then collected by centrifugation (250×g) and re-suspended in HBSS. Viable cells, cells that excluded 0.4% trypan blue, were counted with a hemocytometer; 0-time (seeding) cell counts were deducted from final cell counts to provide an estimate of the net increase in cell number.

The $IC_{50}$ value represents the concentration of an isoprenoid required to inhibit the net increase in cell count by 50% at a time point within the linear growth period plotted for control cells. We determined the $IC_{50}$ value by plotting cell number against isoprenoid concentration.

M364 and lovastatin-initiated changes in cell cycle distribution of HL-60 and B16 cells were monitored by flow cytometry. Cell pellets (>$1 \times 10^6$ cells), harvested as described above, were fixed in 1 mL 70% ethanol at 4° C. for 60 minutes, washed in 1 mL PBS and resuspended in 400 μL PBS containing 0.5 mg RNAse A (Sigma). After gentle mixing a 100 μL aliquot of propidium iodide (1 g/L PBS) (Sigma) was added (Nicoletti, et al., 1991). The cells were incubated in the dark at room temperature for 15 minutes and then held at 4° C. in the dark for flow cytometric analysis. For each sample, at least $1 \times 10^4$ cells were analyzed for DNA content using a flow cytometer (FACSCalibur, Becton Dickinson, San Jose, Calif.). The data acquisition software used for the DNA analysis and distribution of cells in sub-$G_1$, $G_0$-$G_1$, S, and $G_2$-M was CellQuest/ModFit (Verity, Topsham, Me.). The sub-$G_1$ peak is an indicator of the onset of apoptosis (Hotz, M. A., et al., *Cytometry* 15:237–244, 1994).

FIG. 1 shows the structures of M363 [4-(3,7-dimethyl-2,6-octadienyloxy]-phenyl acetate, M364 [4-(3,7,11-trimethyl-2,6,10-dodecatrienyloxy]-phenyl acetate, and farnesyl anthranilate. The $IC_{50}$ values calculated for murine melanoma B16 cells for M363, M364 and farnesyl anthranilate are 5.1±0.8, 2.0±0.6 and 45±6 μmol/L respectively.

The $IC_{50}$ values calculated for human HL-60 promyelocytic leukemia cells M363, M364 and farnesyl anthranilate are 58.6±2.3, 4.9±3.7 and 80±10 μmol/L respectively. M363 and M364 were synthesized using trans, trans farnesol, farnesyl anthranilate, with a blend of trans, trans and cis, trans isomers.

Figure 2:
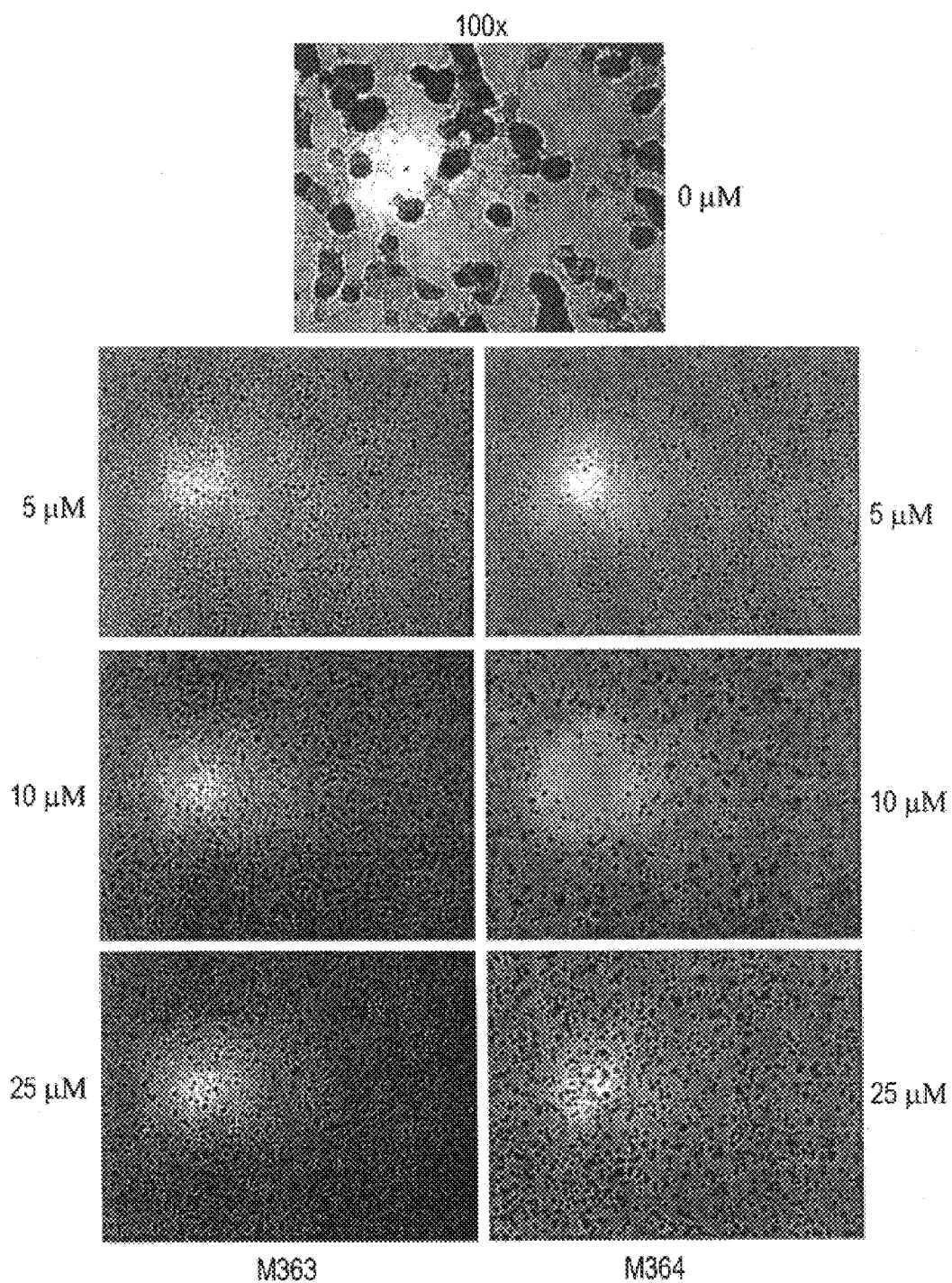
FIG. 2 is a photomicrograph at 100× showing the concentration dependent impact of M363 and M364 on the growth of B16 melanoma cells.
Figure 3:
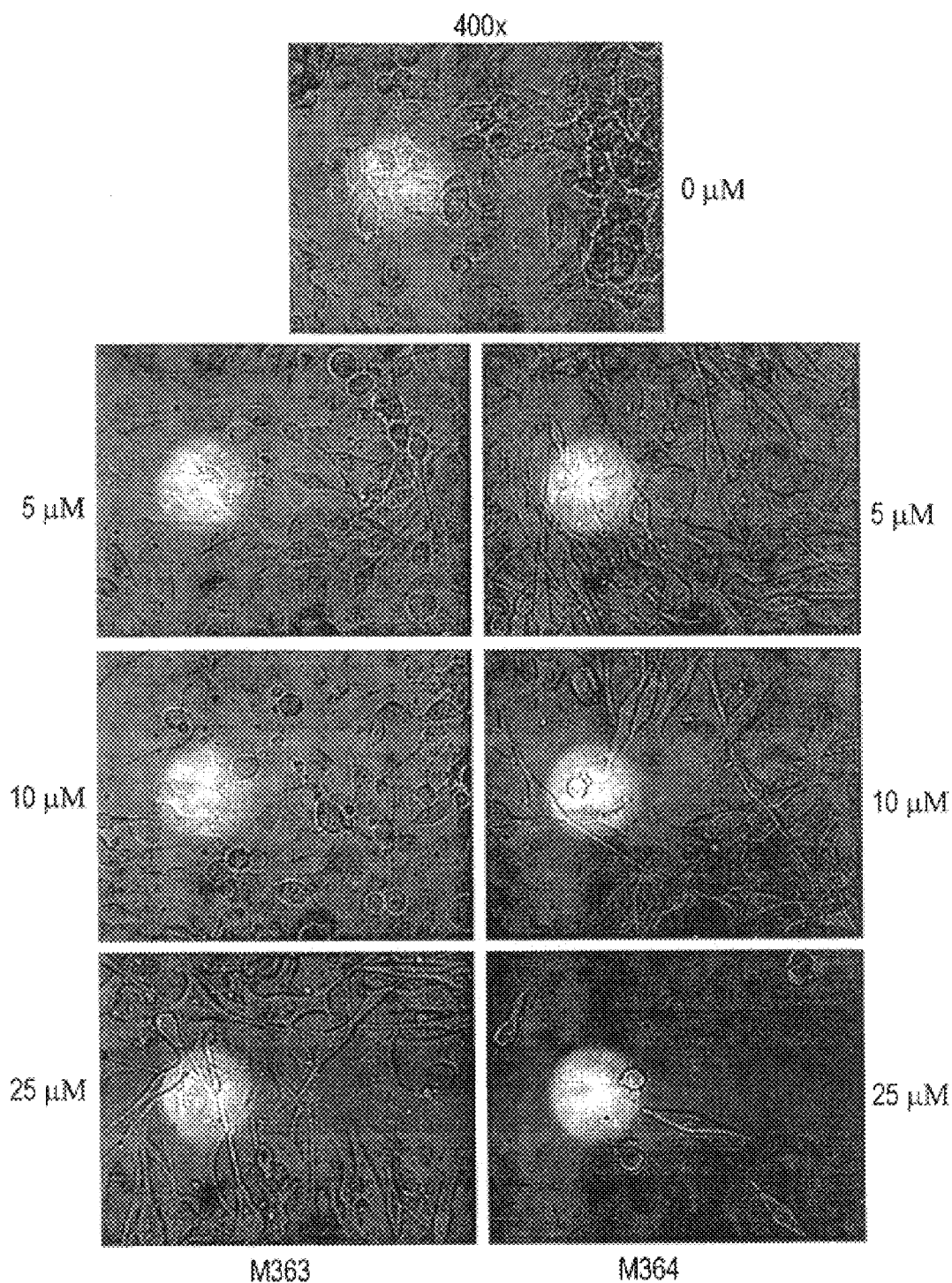
FIG. 3 is a photomicrograph at 400× showing the concentration dependent impact of M363 and M364 on the growth of B16 melanoma cells.
Figure 4:
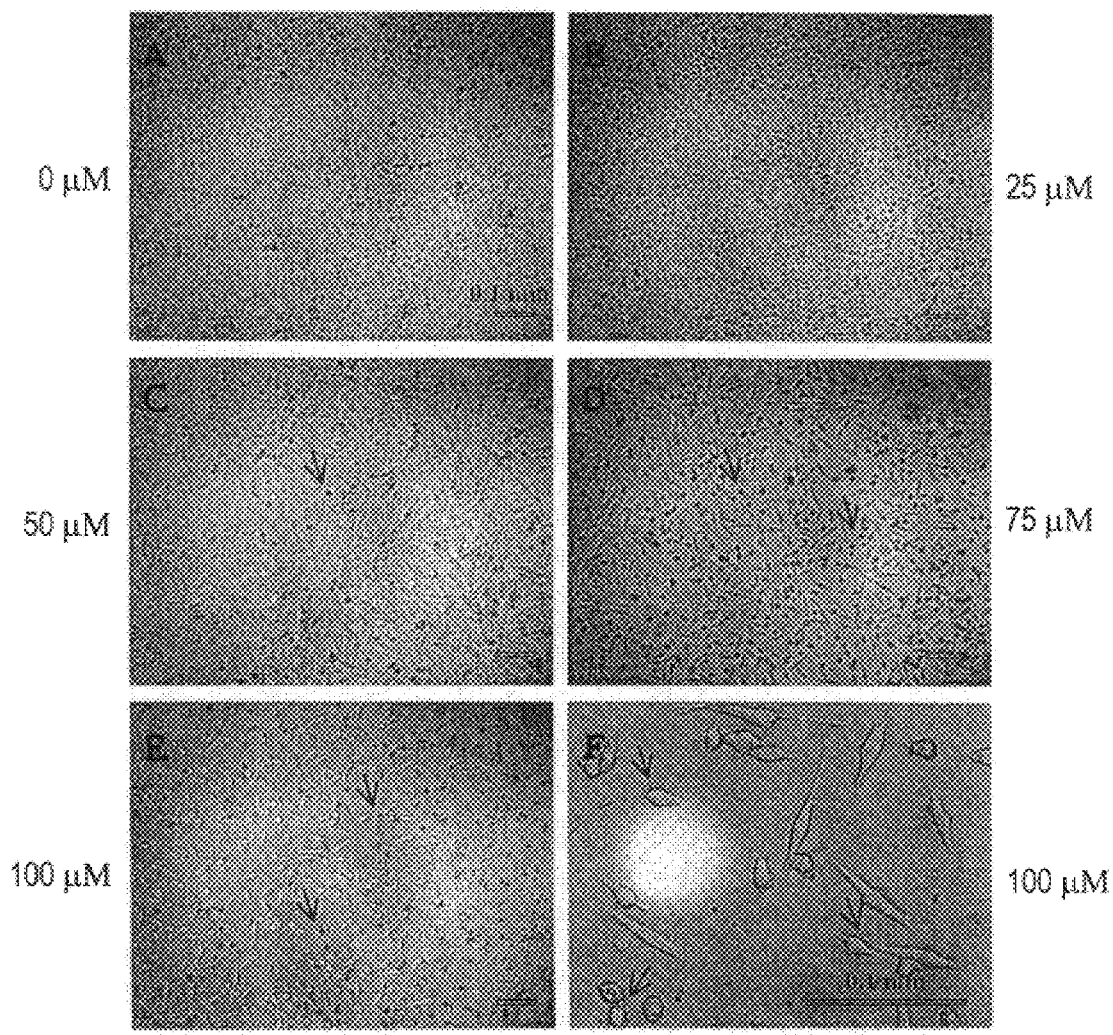

The 100×photomicrographs (FIG. 2) show the concentration-dependent impacts of M363 and M364 on the growth of B16 melanoma cells. Both agents reduced cell number by more than 50% and initiated apoptosis when present at 5 μmol/L. The 400×photomicrographs (FIG. 3) reveals clearly the morphological features of apoptosing cells—rounding up accompanied by the blebbing of the plasma membrane. For comparison, we offer 100× photomicrographs (FIGS. 4A–E) of melanoma B16 cells incubated with farnesyl anthranilate (0–100 μmol/L). The 400×magnification (FIG. 4F) of cells incubated with 100 μmol/L farnesyl anthranilate shows morphological changes similar to those attained with 10 μmol M364.

FIG. 5 shows the impacts of M364 and lovastatin individually and in combination on the growth and cell cycle distribution of murine B16 melanoma cells. Lovastatin (0.75 μmol/L) suppressed cell growth by 25% and increased the portion of cells in G1 by 33%. M364 (1 μmol/L) suppressed cell growth by 45% and increased the proportion of cells in G1 by 33%. The agents in combination suppressed cell growth by 65% and elevated the proportion of G1 cells to 40%. At doubled concentrations, lovastatin and M364 (1.5 and 2 μmol/L respectively), suppressed cell growth by 90% and elevated G1 phase cells by 55%.

Referring to FIG. 5, we envision the combinations will be most effective. FIG. 5 shows additive action of the two agents. The statins have dose-limiting toxicities for normal tissue, and we foresee a combination which incorporates the tumor-specific action of the acyclic isoprenoid ether and the tissue non-specific action of the statins.

Confirmation of $IC_{50}$ for M364 by CellTiter96 Procedure

Murine B16(F10) melanoma cells were grown in monolayer culture (96-well tissue culture plate, Fisher Scientific) in 0.1 mL of RPMI 1640 medium (Sigma) supplemented with 10% fetal bovine serum (Sigma) and 80 mg/L of gentamycin (Sigma). Cultures were seeded in triplicate (0 to 2450 cells/well with an increment of 350 cells) and incubated for 24 hours or 64 hours at 37° C. in a humidified atmosphere of 5% $CO_2$. At 24 hours the medium was decanted from each well and replaced with fresh medium. Cell populations of all wells were determined at either 24 hours (0 time, 3 wells) or 64 hours (40 hours, all other wells) by adding 20 μl of CellTiter 96® Aqueous One Solution (Promega, Madison, Wis.) to each well; the plate was held in dart at 37° C. for 2 hours and then read at 490 nm with a SPECTRAmax® 190 multi-plate reader with SOFTmax® PRO (Molecular Devices, Sunnyvale, Calif.). The net absorbance, the difference between the 0 time and 40 hours values, plotted on cell inoculation density is linear to 2000 cells/well (FIG. 6). We then applied this optical method to the estimation of the $IC_{50}$ for M364.

Plates seeded with 1000 cells/well, the midpoint of cell inoculation density (FIG. 6), were cultured as described above. The medium added at 24 hours (0 time) to experimental wells contained 0–10 μmol/L M364 ([4-(3,7,11-trimethyl-2,6,10-dodecatrienyloxy]-phenyl acetate).

FIG. 7 shows the dose-dependent impact of M364 on the 40 hour growth of B16 melanoma cells. The $IC_{50}$ value determined by the CellTiter 96® Aqueous One Solution Cell Proliferation Assay, 2.2 μmol/L, confirms the value, 2.0±0.6, obtained using the hemocytometer.

M364 toxicity and efficacy studies are in progress. Weanling C57BL6 female mice (Harlan Sprague Dawley, Madison, Wis.) are housed in groups of five to six on Cellu-Dri bedding (Waldschmidt & Sons, Inc., Madison, Wis.) in stainless steel cages and maintained at 25° C. with a 12-hour light:dark cycle. Three groups of mice (11/group) are being fed AIN-93G diet supplemented with 0 (A, control), 1 (B) and 10 (C) mmol M364/kg diet. Food intakes for mice are recorded daily and mice are weighed on alternate days. Results to date are mixed. Mice fed diet C, the diet formulated with 10 mmol M364/kg, remained healthy and active but food intake decreased during a 6 day exposure to the diet. As a consequence, the body weight of these mice decreased from 13.6 to 11.7 g; on removing the agent (M364) from the diet the mice rapidly regained body weight. Body weight and general appearance of mice receiving diet B, the diet formulated with 1 mmol M364/kg, match the controls.

We claim:

1. A method of suppressing the growth of tumor cells in a patient, comprising treating the patient with an effective amount of an isoprenoid ether-linked compound, wherein the isoprenoid ether-linked compound comprises a first acyclic isoprenoid molecule linked via an ether linkage to a second molecule, wherein the second molecule can suppress tumor formation.

2. The method of claim 1 wherein the second molecule comprises a cyclic isoprenoid.

3. The method of claim 1 wherein the second molecule comprises hydroxyphenyl acetate.

4. The method of claim 1 wherein the second molecule comprises 4-hydroxyphenyl acetate.

5. The method of claim 1 wherein the second molecule is a flavonol.

6. The chemotherapeutic compound of claim 5 comprising [4-(3,7,11-trimethyl-2,6,10-dodecatrionyloxy]-phenylacetate and a pharmaceutical carrier.

7. The method of claim 1 wherein the second molecule is an isoflavonol.

8. The method of claim 1 wherein the second molecule is a polyphenol.

9. The method of claim 1 wherein the second molecule is a substituted hydroquinone.

10. The method of claim 1 wherein the first molecule is an acyclic isoprenoid alcohol.

11. The method of claim 1 wherein the treatment of the tumor cell comprises ingestion of the isoprenoid ether-linked compound by a tumor patient.

12. A chemotherapeutic compound comprising an acyclic isoprenoid linked via an ether linkage to a cyclic isoprenoid and a pharmaceutical carrier.

13. A chemotherapeutic compound comprising an acyclic isoprenoid linked via an ether linkage to a hydroxyphenyl acetate.

14. A compound comprising [4-(3,7,11-trimethyl-2,6,10-dodecatrionyloxy]-phenylacetate.

* * * * *

UNITED STATES PATENT AND TRADEMARK OFFICE
CERTIFICATE OF CORRECTION

PATENT NO.    : 6,566,397 B2
DATED         : May 20, 2003
INVENTOR(S)   : Charles E. Elson et al.

It is certified that error appears in the above-identified patent and that said Letters Patent is hereby corrected as shown below:

<u>Column 1,</u>
Line 4, please insert after "Statement Regarding Federally Sponsored Research or Development":

-- This invention was made with United States government support awarded to the following agency: NIH CA 73418. The United States has certain rights in this invention. --

Signed and Sealed this

Seventh Day of October, 2003

JAMES E. ROGAN
*Director of the United States Patent and Trademark Office*